(12) United States Patent
Hayashi et al.

(10) Patent No.: US 6,352,705 B1
(45) Date of Patent: Mar. 5, 2002

(54) FABRIC PROTECTANTS

(75) Inventors: Yoko Hayashi, Toyonaka; Takaaki Itoh, Nishinomiya, both of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 08/062,210

(22) Filed: May 18, 1993

(30) Foreign Application Priority Data

Jun. 26, 1992 (JP) .............................. 4-168898

(51) Int. Cl.$^7$ .............................. A01N 25/10
(52) U.S. Cl. ................. 424/409; 424/403; 424/408; 424/411; 424/412; 424/413; 424/414; 424/416; 424/418; 514/531; 523/122
(58) Field of Search ................. 424/403, 405–413, 424/414, 416, 418; 514/513, 531, 919; 523/122; 2/4

(56) References Cited

U.S. PATENT DOCUMENTS

| 76,342 A | * | 4/1868 | Perkins ........................ 424/413 |
| 3,044,885 A | * | 7/1962 | Loehr ......................... 424/413 |
| 3,719,751 A | * | 3/1973 | Rauscher et al. ........... 424/403 |
| 4,765,982 A | * | 8/1988 | Ronning et al. ............. 424/403 |
| 4,889,872 A | | 12/1989 | Naumann et al. ........... 514/531 |
| 5,198,287 A | * | 3/1993 | Samson et al. ............. 428/248 |

FOREIGN PATENT DOCUMENTS

| AU | B1203788 | 8/1988 |
| DE | 0279325 | 8/1988 |

OTHER PUBLICATIONS

Chemical Patents Index, Documentation Abstracts Journal, Section Ch, Week 9146, Jan. 22, 1992, Derwent Publications Ltd., London, GB; AN 337375, Research Disclosure RD330067A (Oct. 10, 1991), Anonymous.

Chemical Patents Index, Documentation Abstracts Journal, Section Ch, Week 9146, Jan. 22, 1992, Derwent Publications Ltd., London, GB; AN 337387, Research Disclosure RD330379A (Oct. 10, 1991), Anonymous.

Chemical Patents Index, Documentation Abstracts Journal, Section Ch, Week 9115, Jun. 12, 1991, Derwent Publications Ltd., London, GB; AN 107517 & JP–A–03 051 398 (Chuetsu Pulp Kogyo Shum–)) Mar. 5, 1991.

Chemical Patents Index, Documentation Abstracts Journal, Section Ch, Week 8508, Apr. 17, 1985, Derwent Publications Ltd., London, GB; AN 046143 & JP–A–60 002 799 (Dainippon Jochigiku KK) Jan. 9, 1985.

Dziegielewska, "ABC Porzadkow Domowych," Warta, Warszawa 1984, p. 147.

* cited by examiner

Primary Examiner—Neil S. Levy
(74) Attorney, Agent, or Firm—Sughrue, Mion, Zinn, Macpeak & Seas, PLLC

(57) ABSTRACT

A fabric protectant comprising a cellulosic material having a bulk density of 0.2 to 0.7 g/cm$^3$ and a thickness of 0.1 to 4 mm and a composition containing as an active ingredient 2,3,5,6-tetrafluorobenzyl (+)-1R,trans-2,2-dimethyl-3-(2,2-dichlorovinyl)cyclo-propanecarboxylate, said cellulosic material having the composition supported thereon or being impregnated with the composition, which maintains a stable attack-preventing effect over a long period of time.

5 Claims, No Drawings

FABRIC PROTECTANTS

The present invention relates to a protectant for fabrics such as clothes, carpets and the like.

It is disclosed in U.S. Pat. No. 4,889,872 that 2,3,5,6-tetrafluorobenzyl (+)-1R,trans-2,2-dimethyl-3-(2,2-dichlorovinyl)cyclopropanecarboxylate (benfluthrin) has an insecticidal activity.

When benfluthrin is used for protecting fabrics against pest insects, however, it has been difficult to obtain a stable protecting effect over a long period of time.

Generally speaking, the preferred type of fabric protectant is one which has a stable effect over a long period of time, rather than one which has an immediate effect required for extermination of sanitary insects such as flies, mosquitoes, cockroaches and the like. For example, the former type is expected to have an advantage in that the efficacy lasts for at long as half a year, and mere exchange of the protectants will suffice for seasonal change of clothing.

Another property required for a fabric protectant is an attack-preventing effect.

That is, even if an insecticidal effect appears after feeding by pests as in the case of poisonous baits, such a fabric protectant is not regarded as efficacious. What is important in a fabric protectant is that it protects precious clothing against attack by pests, in other words, it has an attack-preventing effect.

The present inventors have done extensive research in an attempt to find a fabric protectant having the aforementioned preferred effects, and as a result, have found that a fabric protectant comprising a cellulosic material having a bulk density of 0.2 to 0.7 g/cm$^3$ and a thickness of 0.1 to 4 mm and a composition containing as an active ingredient benfluthrin, said cellulosic material having the composition supported thereon or being impregnated with the composition satisfies the above object. The present inventors thus attained the present invention.

The object of the present invention is to provide a fabric protectant which has a stable protecting effect against pest insects and attack-preventing effect over a long period of time.

Another object of the present invention is to provide a method for protecting fabrics, which comprises applying the fabric protectant of the present invention to pest insects or fabrics.

Further object of the present invention is to provide a method for controlling pest insects, which comprises applying the fabric protectant of the present invention to pest insects or fabrics.

Other objects and advantages of the present invention will become apparent from the following description.

In accordance with the present invention, there is provided a fabric protectant comprising a cellulosic material having a bulk density of 0.2 to 0.7 g/cm$^3$ and a thickness of 0.1 to 4 mm and a composition containing as an active ingredient benfluthrin, said cellulosic material having the composition supported thereon or being impregnated with the composition.

In producing the fabric protectant of the present invention, benfluthrin may be supported, as it is, on a cellulosic material having a bulk density of 0.2 to 0.7 g/cm$^3$ and a thickness of 0.1 to 4 mm without adding any other ingredient, Usually, however, it is convenient to dissolve benfluthrin in a suitable organic solvent and impregnate or immerse the cellulosic material with or in the resulting solution. The solvent which may be used includes, for example, alcohols (e.g. ethanol), esters (e.g. ethyl acetate), halogenated hydrocarbons (e.g. dichloroethane), ketones (e.g. acetone, methyl ethyl ketone), ethers (e.g. tetrahydrofuran, dioxane), aliphatic hydrocarbons (e.g. hexane, kerosene, paraffin, petroleum benzine), aromatic hydrocarbons (e.g. toluene) and the like. To these solvents may be added usual emulsifiers, dispersing agents, spreading agents, stabilizing agents and the like. Further, protectants other than benfluthrin, antimolding agents, synergists and the like may be added if necessary.

The cellulosic material used in the present invention is such that the bulk density, i.e. weight per definite volume, is 0.2 to 0.7 g/cm$^3$ and the thickness is 0.1 to 4 mm. The cellulosic material includes, for example, cardboard, filter paper, cotton linter and the like, the bulk density and thickness of each of which is in the ranges of the above numerical values. The fabric protectant of the present invention can be applied in the form of sheets, Tablets, etc.

The fabric protectant of the present invention contains as an active ingredient benfluthrin, usually in an amount of 1 to 100 mg/cm$^3$ of the cellulosic material, but this amount may vary depending upon the kind of cellulosic materials, and where, how and when the fabric protectant is applied.

Pest insects which are a target for control by the fabric protectant of the present invention include Tinea spp. such as casemaking clothes moth, etc., Tineola spp. such as webbing clothes moth, etc. and Trichophaga spp. such as carpet moth, etc.

The fabric protectant of the present invention can be used to control pest insects or protect fabrics from pest insects by putting on or hanging in furniture for clothes such as wardrobe, drawer, chest and so on.

The present invention will be illustrated more specifically with reference to the following examples, but it is not to be interpreted as being limited to these examples alone.

First, production examples of the fabric protectant of the present invention will be shown.

PRODUCTION EXAMPLE 1

Fifty millgrams of benfluthrin was coated onto a cellulosic material (cotton linter) of 3.5 cm×2.2 cm×0.28 cm (thick) in size, and 0.39 g/cm$^3$ in bulk density, to obtain a fabric protectant of the present invention.

PRODUCTION EXAMPLE 2

An acetone solution of benfluthrin was coated onto a cellulosic material (filter paper) of 34 cm×58 cm×0.02 cm (thick) in size, and 0.50 g/cm$^3$ in bulk density, so that the amount of benfluthrin was 200 mg, to obtain a fabric protectant of the present invention.

Test examples on pest insects will be shown.

TEST EXAMPLES

Test pieces of 3.2 cm×3.2 cm in size were cut out of cellulosic materials shown in Table 1 described later. An acetone solution of benfluthrin was dropped onto every test piece so that the amount of benfluthrin was 20 mg, and then air-dried, to obtain a fabric protectant. Every fabric protectant obtained was hung from the upper central part of a corrugated cardboard box of 30 cm×30 cm×30 cm in size. Three spherical wire-net cages of 5 cm in diameter, each cage containing 10 larvae of webbing clothes moth and one piece of woolen fabric, 2 cm×2 cm in size, were set in the upper part of the box. The inner part of the box was kept air-tight, and after one week, the degree of attack on the piece of woolen fabric was observed. The same test was repeated after 2, 4, 8, 16 and 24 weeks. The results are shown in Table 1. In the table, the attack-preventing effect was indicated according to the following criterion:

TABLE 1

| | Cellulosic material | | Period of time elapsed (week)/ Attack preventing effect | | | | | |
|---|---|---|---|---|---|---|---|---|
| | Bulk density ($g/cm^3$) | Thickness (mm) | 0 | 2 | 4 | 8 | 16 | 24 |
| Test Example 1 | 0.50 | 0.23 | ○ | ○ | ○ | ○ | ○ | ○ |
| Test Example 2 | 0.39 | 2.80 | ○ | ○ | ○ | ○ | ○ | ○ |
| Test Example 3 | 0.31 | 0.15 | ○ | ○ | ○ | ○ | ○ | ○ |
| Comparative Example 1 | 0.12 | 4.40 | ○ | ○ | Δ | Δ | × | × |
| Comparative Example 2 | 0.82 | 0.57 | ○ | ○ | ○ | Δ | Δ | × |
| Comparative Example 3 | 0.74 | 0.07 | ○ | ○ | Δ | × | × | × |
| Comparative Example 4 | 0.44 | 0.03 | Δ | × | × | × | × | × |

○: No attack.
Δ: Attack is observed partially.
×: Attack is observed.

In Test Examples 1, 2 and 3 using the fabric protectants of the present invention, a stable attack-preventing effect was observed over a long period of 24 weeks.

On the other hand, in Comparative Examples 1 to 4, the fabric protectants were prepared with cellulosic materials which had a different bulk density and/or thickness from those used in the fabric protectants of the present invention. As a result, it was observed that the residual effect over a long period of time was not sufficient.

As the results in Table 1 show, the fabric protectant of the present invention has a stable attack-preventing effect over a long period of time.

What is claimed is:

1. A method for protecting clothes, which comprises placing in the vicinity of said clothes a clothes protectant, wherein said clothes protectant comprises a cellulosic material having a bulk density of 0.2 to 0.7 $g/cm^3$ and a thickness of 0.1 to 4 mm and a composition containing 2,3,5,6-tetrafluorobenzyl (+)-1R,trans-2,2-dimethyl-3-(2,2-dichlorovinyl) cyclopropanecarboxylate as an active ingredient, said cellulosic material either having the composition supported thereon or being impregnated with the composition.

2. The method according to claim 1, wherein the clothes protectant is put on or hung in furniture for clothes.

3. The method according to claim 1, wherein the amount of the active ingredient is 1 to 100 $mg/cm^3$ of the cellulosic material.

4. A method for controlling clothes pest insects, which comprises placing in the vicinity of said clothes a clothes protectant, wherein said clothes protectant comprises a cellulosic material having a bulk density of 0.2 to 0.7 $g/cm^3$ and a thickness of 0.1 to 4 mm and a composition containing 2,3,5,6-tetrafluorobenzyl (+)-1R,trans-2,2-dimethyl-3-(2,2-dichlorovinyl)cyclopropanecarboxylate as an active ingredient, said cellulosic material either having the composition supported thereon or being impregnated with the composition.

5. The method according to claim 4, wherein the amount of the active ingredient is 1 to 100 $mg/cm^3$ of the cellulosic material.

* * * * *